(12) United States Patent
Choi et al.

(10) Patent No.: US 12,742,727 B2
(45) Date of Patent: Sep. 22, 2026

(54) AIR QUALITY MEASURING DEVICE

(71) Applicant: SAMSUNG ELECTRONICS CO., LTD., Suwon-si (KR)

(72) Inventors: Junghui Choi, Suwon-si (KR); Keunbum Lee, Suwon-si (KR); Changwoo Jung, Suwon-si (KR); Buyoun Lee, Suwon-si (KR); Changheon Lee, Suwon-si (KR); Sangki Cho, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 204 days.

(21) Appl. No.: 18/664,157

(22) Filed: May 14, 2024

(65) Prior Publication Data

US 2024/0302268 A1 Sep. 12, 2024

Related U.S. Application Data

(63) Continuation of application No. PCT/KR2022/019781, filed on Dec. 7, 2022.

(30) Foreign Application Priority Data

Feb. 3, 2022 (KR) ........................ 10-2022-0014109

(51) Int. Cl.
*G01N 21/21* (2006.01)
*G01N 21/29* (2006.01)
(Continued)

(52) U.S. Cl.
CPC ......... *G01N 21/29* (2013.01); *G01N 33/0047* (2013.01); *G01N 2021/216* (2013.01);
(Continued)

(58) Field of Classification Search
CPC ............. G01N 15/0205; G01N 15/075; G01N 21/29; G01N 33/0047; G01N 2021/216;
(Continued)

(56) References Cited

U.S. PATENT DOCUMENTS

| | | | | |
|---|---|---|---|---|
| 4,868,384 A * | 9/1989 | Franken | H03K 17/18 | 250/221 |
| 2014/0211497 A1* | 7/2014 | Yuan | G02B 6/002 | 362/555 |
| 2019/0208095 A1* | 7/2019 | Kraz | G02B 6/0051 | |
| 2021/0372584 A1* | 12/2021 | Tai | F21S 41/143 | |

FOREIGN PATENT DOCUMENTS

| | | | |
|---|---|---|---|
| CN | 208817386 U * | 5/2019 | F21S 43/243 |
| JP | 6995507 B2 | 1/2022 | |

(Continued)

OTHER PUBLICATIONS

Search English translation of CN 208817386 U (Year: 2019).*
(Continued)

*Primary Examiner* — Omar Rojas Cadima
(74) *Attorney, Agent, or Firm* — CANTOR COLBURN LLP

(57) ABSTRACT

An air quality measuring device, according to one embodiment of the present disclosure, includes a top case, a bottom case provided below the top case, a circular light guide unit which is disposed between the top case and the bottom case. The air quality measuring device has an outer portion and an inner portion, and includes a coupling boss positioned around the outer portion so as to be coupled to the top case or the bottom case. The air quality measuring device also includes a light source unit positioned on the inner portion, where the light guide unit has a light exit surface formed on the outer portion and may include a rib which is positioned around the outer portion and protrudes from one surface thereof.

16 Claims, 14 Drawing Sheets

(51) Int. Cl.
*G01N 33/00* (2006.01)
*G01N 21/85* (2006.01)

(52) U.S. Cl.
CPC ................ *G01N 2021/8578* (2013.01); *G01N 2201/0221* (2013.01)

(58) Field of Classification Search
CPC .............. G01N 2021/8578; G01N 2201/0221; G01N 2015/0046; G01N 21/85; G01N 33/00; G01N 21/3504; G01N 21/53; G01N 21/17; G01N 15/0211; G01N 33/004; G01N 2015/0096; G01N 2021/4759; G01D 21/02; G02B 6/002; G02B 6/0035; G02B 6/0038; G02B 6/0036; G02B 6/0043; G02B 6/0045; G02B 6/0046; G02B 6/0048; G02B 6/0033; G02B 6/0011; F21K 9/61; H01H 19/025; F21Y 2115/10; F24F 2221/02; F24F 11/52; F24F 8/10; F24F 8/90; F24F 8/80; F24F 8/20; F24F 8/30; F24F 8/40; F24F 8/50; F24F 8/60; F24F 8/70; H05B 45/00; H05B 45/20; F21V 33/0088; H03K 17/18; Y02B 30/70; Y10T 74/2084
See application file for complete search history.

(56) References Cited

FOREIGN PATENT DOCUMENTS

| | | | |
|---|---|---|---|
| KR | 100625617 | B1 | 9/2006 |
| KR | 101128090 | B1 | 3/2012 |
| KR | 200477918 | Y1 | 8/2015 |
| KR | 101625133 | B1 | 6/2016 |
| KR | 20160062501 | A | 6/2016 |
| KR | 20170002537 | A | 1/2017 |
| KR | 20170034466 | A | 3/2017 |
| KR | 101785357 | B1 | 10/2017 |
| KR | 20170112728 | A | 10/2017 |
| KR | 101912624 | B1 | 10/2018 |
| KR | 101975054 | B1 | 5/2019 |
| KR | 102043612 | B1 | 11/2019 |
| KR | 102273731 | B1 | 7/2021 |
| KR | 20220007355 | A | 1/2022 |
| WO | 2015171571 | A2 | 11/2015 |

OTHER PUBLICATIONS

International Search Report and Written Opinion for International Application No. PCT/KR2022/019781; International Filing Date Dec. 7, 2022; Date of Mailing Mar. 14, 2023, 9 Pages.

Korean Office Action Issued In KR Application No. 10-2022-0014109; Mail Date Feb. 26, 2026; 16 Pages.

* cited by examiner (a)

(b)

AIR QUALITY MEASURING DEVICE

CROSS-REFERENCE TO RELATED APPLICATIONS

This application is a continuation application, claiming priority under § 365(c), of International Application No. PCT/KR2022/019781 filed on Dec. 7, 2022, which is based on and claims the benefit of Korean patent application number 10-2022-0014109 filed on Feb. 3, 2022, in the Korean Intellectual Property Office, the disclosures of which are incorporated by reference herein in their entireties.

BACKGROUND

Various embodiments of the disclosure relate to an air quality measuring device.

Substances harmful to the human body, such as fine dust, harmful gases, or pollutants, may exist floating in the air both outdoors and indoors. These harmful substances are designated as air pollutants that can cause fatal respiratory or infectious diseases. Substances that may be harmful to the human body include fine dust with a diameter of 10 μm or less, ultra-fine dust with a diameter of 2.5 μm or less, volatile organic compounds (VOCs), carbon monoxide, formaldehyde, nitrogen dioxide, sulfur dioxide, ozone, and carbon dioxide.

As consumers become increasingly concerned about harmful substances in the air, air quality monitoring devices that provide comprehensive assessments of the air quality condition not only outdoors but also indoors, such as in homes, offices, or public facilities, are becoming more popular.

In particular, air quality measuring devices used indoors may come in compact size to be highly portable so that users may freely move them to their desired location. Air quality measuring devices generally include a display device to provide information about air quality to users. Accordingly, a user is able to look at the air quality measuring device and identify the air quality via the display device.

SUMMARY

Various embodiments of the disclosure may provide a coupling structure of a light guide that prevents damage to the exterior when disassembled in an air quality measuring device indicating the degree of air pollution using a light color.

Various embodiments of the disclosure may provide a light guide structure capable of compensating for deterioration of luminance uniformity as a coupling boss is positioned at a portion close to the surface where a light color corresponding to the degree of air pollution exits in an air quality measuring device.

An air quality measuring device according to an embodiment of the disclosure includes an upper case, a lower case provided under the upper case, a circular light guide disposed between the upper case and the lower case, having an outer portion and an inner portion, and having a coupling boss positioned around the outer portion to couple with the upper case or the lower case, and a light source unit positioned on the inner portion. The light guide may include a rib having a light exiting surface formed on the outer portion and formed to protrude to one surface around the outer portion.

A circular light guide according to an embodiment of the disclosure may include an inner portion having a light entering surface through which light enters, an outer portion having a light exiting surface through which light exits, a coupling boss positioned around the outer portion and provided to protrude upward or downward, and a rib formed to protrude to one surface around the outer portion.

According to various embodiments proposed in the disclosure, the air quality measuring device may prevent damage to the exterior of the air quality measuring device by being sequentially disassembled from a lower component due to a coupling structure in which a head portion of a screw where a light guide is coupled to an upper case and a head portion of a screw where the light guide is coupled to a lower case are positioned on a lower side.

According to various embodiments proposed in the disclosure, the air quality measuring device may enhance luminance uniformity of a light emitting surface by dispersing the light concentrated on a coupling boss by providing a circumference rib at an outer side of the coupling boss formed for screw coupling.

BRIEF DESCRIPTION OF THE DRAWINGS

The above and other exemplary embodiments, advantages and features of this disclosure will become more apparent by describing in further detail exemplary embodiments thereof with reference to the accompanying drawings, in which.

DETAILED DESCRIPTION

Figure 1:
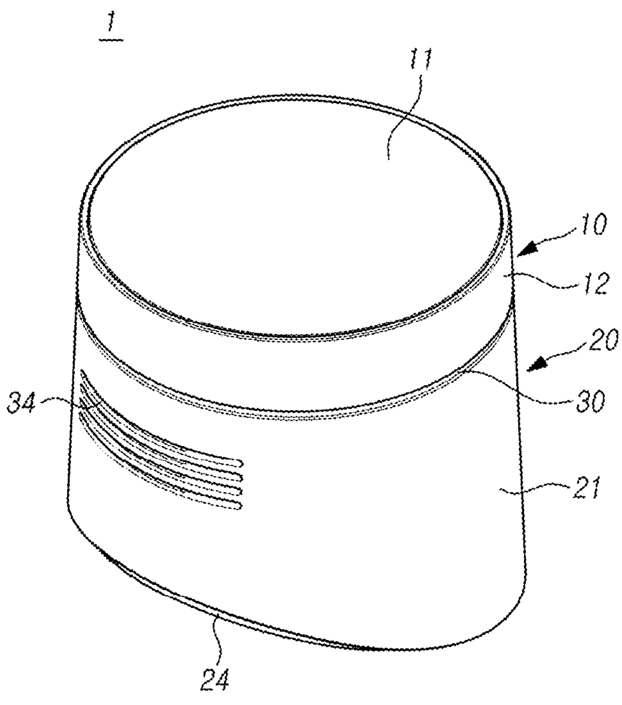
FIG. 1 is a perspective view illustrating an air quality measuring device according to an embodiment of the disclosure.

Embodiments of the present invention are now described with reference to the accompanying drawings in such a detailed manner as to be easily practiced by one of ordinary skill in the art. However, the disclosure may be implemented in other various forms and is not limited to the embodiments set forth herein. The same or similar reference denotations may be used to refer to the same or similar elements throughout the specification and the drawings. Further, for clarity and brevity, no description is made of well-known functions and configurations in the drawings and relevant descriptions.

FIG. 1 is a perspective view illustrating an air quality measuring device according to an embodiment of the disclosure.

In one embodiment, the air quality measuring device 1 is a device that provides a user with information about air quality measured in an indoor environment such as a house, an office, or a public facility. The air quality measuring device 1 may display information about the carbon dioxide concentration, the fine dust concentration, and the organic active material concentration on a display.

The air quality measuring device 1 may provide intuitive information about air quality to the user by emitting light various colors according to the air quality steps. For example, the air quality measuring device 1 may vary the light color of the light source unit (e.g., the light source unit 40 of FIG. 3) so as to vary the light color emitted from a light exiting surface 321 (shown in FIG. 2) of the light guide 30 according to the measured air quality. For example, when the air quality steps are divided into five steps of very good, good, normal, bad, and very bad, the controller (e.g., the controller 100 of FIG. 4) may display blue (good), green (normal), yellow (bad), and red (very bad) on the light exiting surface 321 of the light guide 30 according to each step using the light source unit (e.g., the light source unit 40 of FIG. 3). As will be appreciated by those of ordinary skill in the art, the number of steps and the specific colors according to the steps are exemplary, and may be variously determined according to design or user settings.

In one embodiment, the air quality measuring device 1 may have a substantially cylindrical shape. The air quality measuring device 1 may have an inclined planar lower surface. Accordingly, the air quality measuring device 1 may be disposed so that the display 90 (shown in FIGS. 2 and 3) disposed on the upper surface is disposed in an upward inclined direction when placed on a flat space, allowing the user to more easily identify the information displayed on the display 90. According to an embodiment, the lower cover 24 is positioned on a lower surface of the air quality measuring device 1. In one embodiment, the lower cover 24 may include a mounting unit, and may be used as a wall hanger by the mounting unit. In other words, the lower cover 24 may be used as a wall hanger so that the lower surface having an inclined plane faces the wall.

The air quality measuring device 1 may transfer information about the measured indoor air quality to other peripheral devices. In other words, the air quality measuring device 1 may transmit and receive signals to and from other electronic products or control other electronic products using wireless communication. For example, the air quality measuring device 1 may be configured to interact with an air purifier disposed in the house to operate the air purifier when the concentration of a harmful substance such as indoor fine dust, carbon dioxide, or harmful gas exceeds a predetermined concentration.

Figure 2:
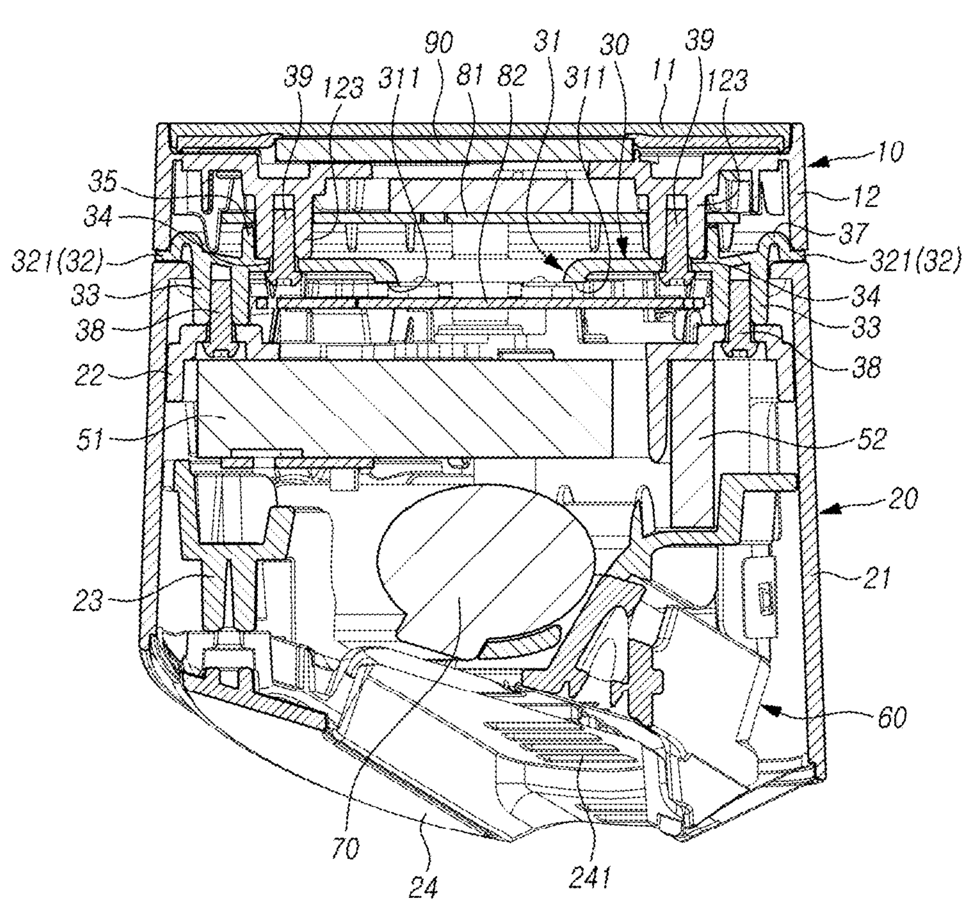
FIG. 2 is a cross-sectional view illustrating an air quality measuring device according to an embodiment of the disclosure.
Figure 3:
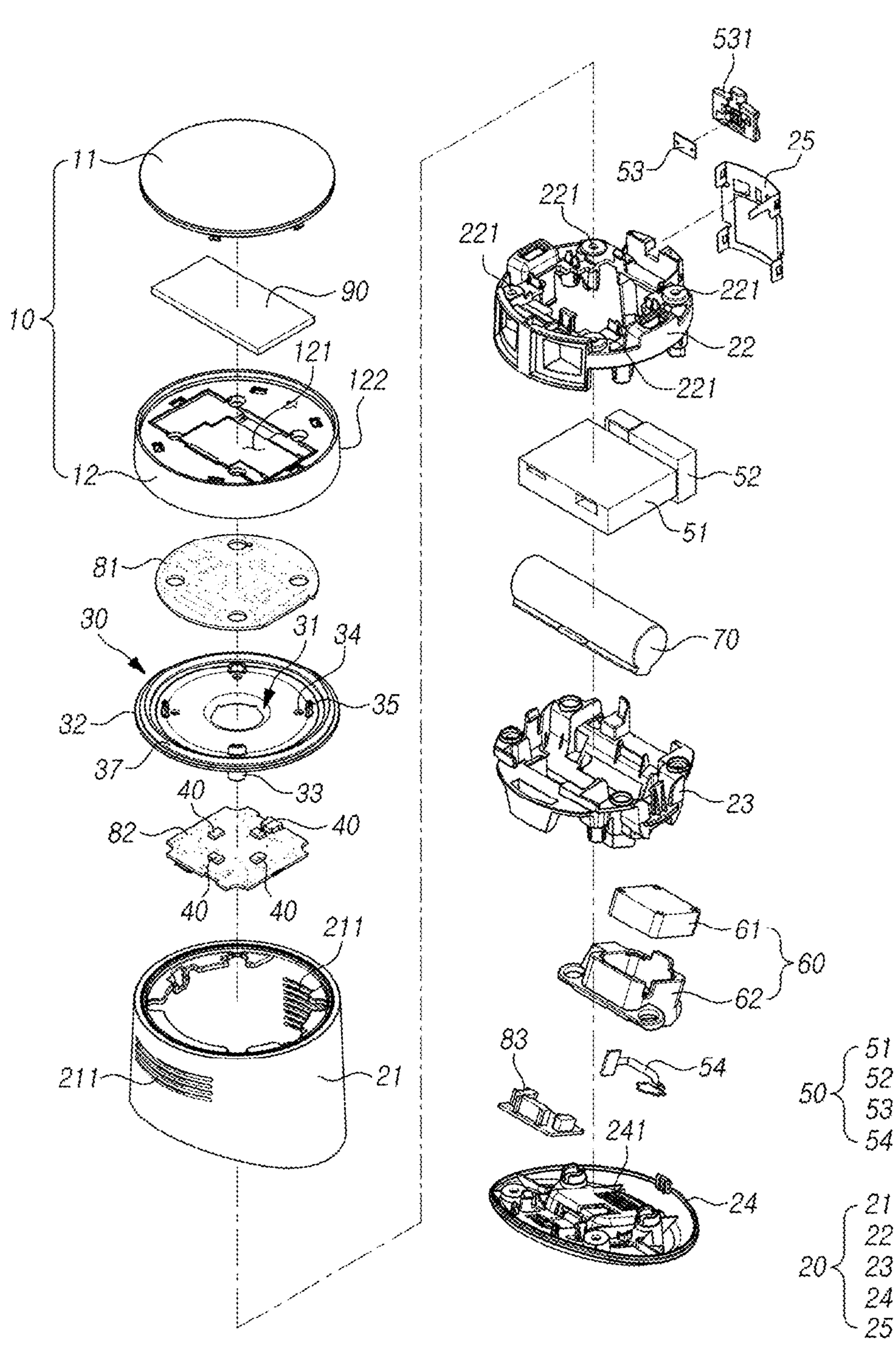
FIG. 3 is an disassembled perspective view illustrating an air quality measuring device according to an embodiment of the disclosure.
Figure 4:
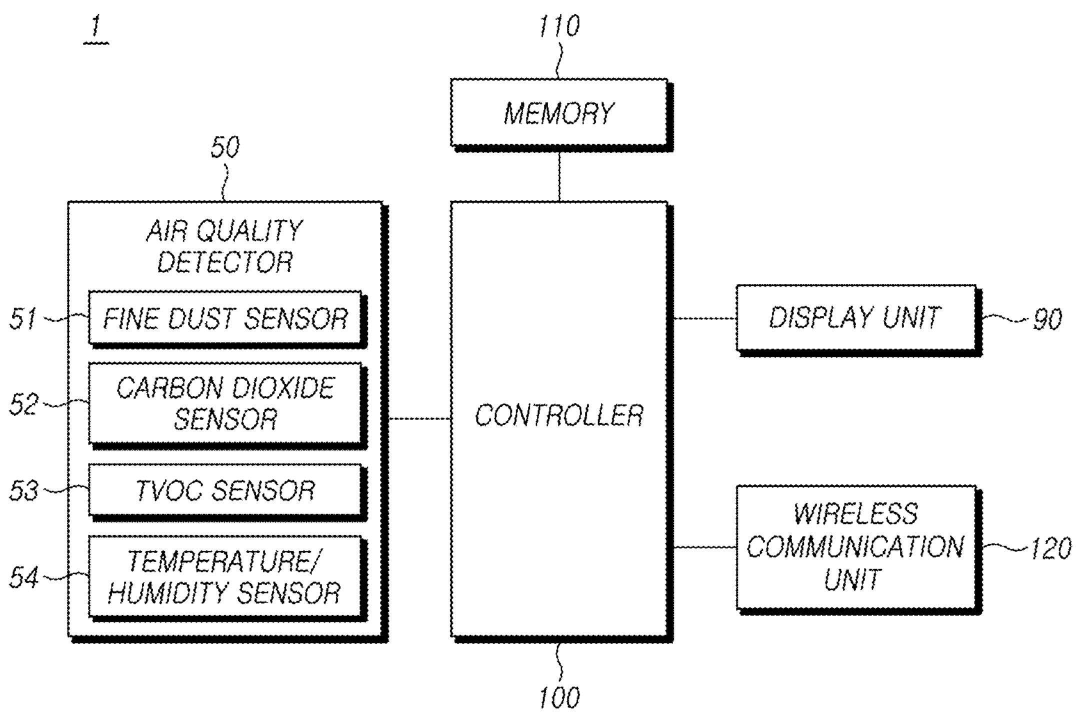
FIG. 4 is a block diagram illustrating an air quality measuring device according to an embodiment of the disclosure.

FIG. 2 is a cross-sectional view illustrating an air quality measuring device according to an embodiment of the disclosure. FIG. 3 is a disassembled perspective view illustrating an air quality measuring device according to an embodiment of the disclosure. FIG. 4 is a block diagram illustrating an air quality measuring device according to an embodiment of the disclosure.

Referring to FIGS. 2 and 3, the air quality measuring device 1 may include an upper case 10, a lower case 20, a light guide 30, a light source 40, a display 90, and a battery 70.

According to an embodiment, the upper case 10 may include a window 11 or an upper frame 12. The upper case 10 may have a cylindrical shape with an open lower portion as a whole. The open lower portion of the upper case 10 may be provided with the light guide 30.

According to an embodiment, the window 11 may be provided to form an upper surface of the upper case 10. The window 11 may be formed of a transparent material. Accordingly, the user may identify the information displayed on the display 90 through the window 11. The window 11 may be formed in a circular shape.

According to an embodiment, the upper frame 12 may have an upper receiving space 121 therein. For example, the display 90 or the first substrate 81 may be disposed in the upper receiving space 121. The upper frame 12 may be formed to fix the display 90 or the first substrate 81. Here, a controller (the controller 100 of FIG. 4) may be mounted on the first substrate 81. The first substrate 81 may be disposed between the upper frame 12 and the light guide 30. Accordingly, the first substrate 81 may have a hole through which a screw may pass at a portion corresponding to where the upper frame 12 and the light guide 30 are screw-coupled.

According to an embodiment, the upper frame 12 may include an upper outer circumferential surface 122 or an upper coupling boss 123. The upper outer circumferential surface 122 may form a portion of the exterior of the air quality measuring device 1. The upper outer circumferential surface 122 may be cylindrical. The upper coupling boss 123 may be formed to protrude downward of the upper frame 12. The upper coupling boss 123 may be positioned at a position corresponding to a coupling hole 34 of the light guide 30. The upper coupling boss 123 may be provided for screw coupling with the light guide 30. As many upper coupling bosses 123 as the number of coupling holes 34 may be provided.

According to an embodiment, the light guide 30 may be provided between the upper case 10 and the lower case 20. The light guide 30 may be circular. The cross-sectional area of the light guide 30 may correspond to the size of the cross-sectional area of the portion in contact with the light guide 30 in the upper case 10. The light guide 30 may be coupled between the upper case 10 and the lower case 20 so that the outer portion 32 may be visible from the outside. The outer portion 32 of the light guide 30 may include a light exiting surface 321. The air quality measuring device 1 may emit light of various colors according to the air quality steps from the light exiting surface 321 of the light guide 30 so that the user may intuitively identify information about the air quality.

According to an embodiment, the light guide 30 may include a coupling boss 33 and/or a coupling hole 34. The light guide 30 may be fastened between the upper case 10 and the lower case 20 using one or more of the coupling boss 33 and the coupling hole 34.

According to an embodiment, the coupling boss 33 may be formed to protrude upward or downward to be coupled to the upper case 10 or the lower case 20. Specifically, the coupling boss 33 may protrude downward to be coupled to the lower case 20 as illustrated. A plurality of coupling bosses 33 may be provided to be spaced apart from each other by predetermined intervals. In one embodiment, four coupling bosses 33 may be disposed to be spaced apart from each other by predetermined intervals.

The coupling bosses 33 may be positioned around the outer portion 32 of the light guide 30. In other words, the coupling bosses 33 may be disposed close to the outer portion 32 of the light guide 30. The light guide 30 may be coupled to the lower case 20 by fastening the first screw 38 from the lower side to the upper side. In other words, the light guide 30 and the lower case 20 may be coupled to each other by allowing the head portion of the first screw 38 to face downward.

According to an embodiment, the coupling hole 34 may be provided to be coupled to the upper case 10. The coupling hole 34 may be provided further inside of the light guide 30 than the coupling boss 33. In other words, the coupling hole 34 may be positioned further away from the outer portion 32 of the light guide 30 than the coupling boss 33. However, the disclosure is not limited thereto, and the coupling hole 34 may be positioned outside the coupling boss 33. The coupling hole 34 and the coupling boss 33 may be positioned to be spaced apart along a radial direction of the light guide 30. A plurality of coupling holes 34 may be provided to be spaced apart from each other by a predetermined interval. The number of coupling holes 34 may correspond to the number of coupling bosses 33, but is not limited thereto.

The light guide 30 may be coupled to the upper case 10 by fastening the second screw 39 from the lower side to the upper side. In other words, the light guide 30 and the upper case 10 may be coupled to each other by allowing the head portion of the second screw 39 to face downward.

As described above, in the disclosure, when the light guide 30 is coupled to the upper case 10 positioned thereabove and the lower case 20 positioned thereunder, screws (the first screw 38 and the second screw 39) may be fastened from the lower portion to the upper portion, and thus each component may be sequentially disassembled from the lower portion during product disassembly. Conventionally, the screw is disposed from the upper portion to the lower portion for the light guide 30 to be coupled to the upper case 10, so that the upper frame 12 and the light guide 30 need to be separated after separating the window 11 of the upper case 10 during disassembly. In the process of separating the window 11, a tool such as a flat head screw driver is used. In this case, the exterior of the window 11 or the upper case 10 (e.g., the upper outer circumferential surface 122 of the upper frame 12) may be damaged. In the disclosure, since the window 11 is not first separated when the upper case 10 and the light guide 30 are disassembled, it is possible to prevent external damage during disassembly.

According to an embodiment, the light guide 30 may further include a boss guide 35. The boss guide 35 may be positioned adjacent to the coupling hole 34. The boss guide 35 may protrude upward, for example. The boss guide 35 may guide the upper coupling boss 123 so that the upper coupling boss 123 is aligned with the coupling hole 34 so as to couple the light guide 30 and the upper frame 12.

According to an embodiment, the lower case 20 may include a side cover 21, a lower cover 24, a first lower frame 22, a second lower frame 23, and a rear plate 25. The lower case 20 may have a cylindrical shape with an open upper portion as a whole. The lower case 20 may have an inclined lower surface. The light guide 30 may be provided on the upper portion of the lower case 20.

The battery 70, an air quality detector 50, a second substrate 82, and a third substrate 83 may be disposed in an inner space of the lower case 20, but is not limited thereto. In one embodiment, at least one light source unit 40 for irradiating light to an inner portion of the light guide 30 may be mounted on the upper surface of the second substrate 82.

The third substrate 83 may be a power substrate for supplying power. According to an embodiment, all or some of the above-described first substrate 81, second substrate 82, and third substrate 83 may be integrally formed.

The side cover 21 and the lower cover 24 may constitute a partial appearance of the air quality measuring device 1. A power supply (not shown) may be provided in the lower cover 24. The user may turn on/off the air quality measuring device 1 using the power supply. According to an embodiment, the side cover 21 or the lower cover 24 may be provided with a side ventilation hole 211 or a lower ventilation hole 241 to allow outside air to be introduced or discharged into/from the inside the air quality measuring device 1.

The first lower frame 22 and the second lower frame 23 may be surrounded by the side cover 21 and the lower cover 24. The first lower frame 22 may be positioned above the second lower frame 23. The first lower frame 22 may be coupled to the light guide 30. A first coupling hole 221 may be formed in the first lower frame 22 at a position corresponding to the coupling boss 33 of the light guide 30. The coupling boss 33 of the light guide 30 and the first coupling hole 221 of the first lower frame 22 may be coupled by the first screw 38. When coupled, the second substrate 82 may be positioned between the first lower frame 22 and the light guide 30. Similarly, the lower end of the first lower frame 22 and the upper end of the second lower frame 23 may be coupled by screw coupling.

The rear plate 25 may be provided behind the first lower frame 22. The rear plate 25 may be provided adjacent to the side ventilation hole 211 of the side cover 21. The rear plate 25 may be provided to partially surround a Total Volatile Organic Compound (TVOC) sensor 53.

The first lower frame 22 and the second lower frame 23 may be provided to fix components such as the battery 70 or various sensors 51, 52, 53, and/or 54 therein. The battery 70 may be seated on and fixed to the second lower frame 23.

According to an embodiment, the light source unit 40 may be provided in the inner portion 31 of the light guide 30. Specifically, a plurality of light source units 40 may be provided along a light entering surface 311 of the inner portion 31. A plurality of light source units 40 may be disposed to be spaced apart from each other at regular intervals. As illustrated, four light source units 40 may be arranged at regular intervals in the circumferential direction along the light entering surface 311 of the inner portion 31, but are not limited thereto. The light source unit 40 may be a light emitting diode (LED).

According to an embodiment, the display 90 may be provided on the upper surface of the upper case 10. Specifically, the display 90 may be provided under the window 11 of the upper case 10. The window 11 is formed of a transparent material and may protect the display 90 from an external impact. The display 90 may provide visual information to the user by displaying values measured by various sensors 51, 52, 53, and/or 54.

According to an embodiment, the air quality measuring device 1 may further include a fan assembly 60. The fan assembly 60 may be provided to smoothly circulate air into the air quality measuring device 1. The fan assembly 60 may be disposed in the lower case 20. Specifically, the fan assembly 60 may be disposed adjacent to the lower ventilation hole 241 of the lower cover 24.

According to an embodiment, the fan assembly 60 may further include a fan driver 61 and a fan frame 62. The fan driver 61 may be fixed by the fan frame 62. The fan frame 62 may be coupled to the second lower frame 23, but is not limited thereto, and may be integrally formed with the first lower frame 22 or the second lower frame 23.

The block diagram of FIG. 4 is a diagram illustrating electronic devices in the air quality measuring device 1 interacting with the controller 100. The components of FIG. 4 may also be included in the air quality measuring device 1 of FIGS. 1 to 3. The components illustrated in FIG. 4 may be disposed inside the upper case 10 or the lower case 20 of FIGS. 1 to 3.

Referring to FIG. 4, the air quality measuring device 1 may include an air quality detector 50, a display 90, a controller 100, a memory 110, or a wireless communication unit 120.

According to an embodiment, the air quality detector 50 may include a fine dust sensor 51, a carbon dioxide sensor 52, a TVOC sensor 53, or a temperature/humidity sensor 54. However, the disclosure is not limited thereto, and various types of sensors for determining air quality may be provided. According to an embodiment, the air quality detector 50 may also include an ultraviolet sensor for measuring ultraviolet rays. The air quality detector 50 may be disposed inside the lower case 20 to measure air quality based on air introduced through the ventilation hole (the side ventilation hole 211 or the lower ventilation hole 241 of FIG. 3) of the lower case 20.

The fine dust sensor 51 may measure the concentration of fine dust in the air. The fine dust sensor 51 may be implemented as an optical sensor that measures fine dust of various sizes such as PM10 (fine dust less than 10 micrometers), PM2.5 (fine dust less than 2.5 micrometers), PM1.0 (fine dust less than 1.0 micrometers) through scattering of light (laser). The fine dust sensor 51 may measure the concentration of fine dust in a manner of measuring the light emitted into the air and scattered, refracted, or reflected by dust particles by adopting an optical method. Alternatively, the fine dust sensor 51 may measure the concentration of fine dust in a manner of measuring the angle of laser beams emitted into the air and reflected by fine dust, but the measurement method of the fine dust sensor 51 is not limited thereto.

According to an embodiment, the fine dust sensor 51 may be disposed inside the lower case 20. The fine dust sensor 51 may be fixedly disposed by the first lower frame 22. The fine dust sensor 51 may be disposed above the battery 70. The placement of the fine dust sensor 51 is exemplary and is not limited thereto.

The carbon dioxide sensor 52 may measure the concentration of carbon dioxide in the air. The carbon dioxide sensor 52 may detect the concentration of carbon dioxide by a non-dispersive infrared absorption method, but is not limited thereto.

According to an embodiment, the carbon dioxide sensor 52 may be disposed inside the lower case 20. The carbon dioxide sensor 52 may be fixedly disposed by the first lower frame 22. The carbon dioxide sensor 52 may be disposed adjacent to the fine dust sensor 51. The placement of the carbon dioxide sensor 52 is exemplary and is not limited thereto.

The temperature/humidity sensor 54 may measure, in real time, the temperature and humidity of the place where the air quality measuring device 1 is installed. The controller 100 may more accurately derive the fine dust concentration and the TVOC concentration at the installation site using the information about the temperature and humidity received from the temperature/humidity sensor 54. According to an embodiment, the temperature/humidity sensor 54 may be configured of separate components, i.e., a temperature sensor and a humidity sensor.

According to an embodiment, the temperature/humidity sensor 54 may be disposed inside the lower case 20. The temperature/humidity sensor 54 may be disposed adjacent to the lower ventilation hole 241 of the lower cover 24. Accordingly, the temperature/humidity sensor 54 may measure the temperature and humidity of the air introduced into the lower ventilation hole 241. The placement of the temperature/humidity sensor 54 is exemplary and is not limited thereto.

The TVOC sensor 53 may measure the concentration of the total volatile organic compound (TVOC) in the air. The TVOC sensor 53 may measure the concentration of harmful gases. Specifically, the TVOC sensor 53 may measure the concentration of harmful gases in the air introduced into the lower case 20. TVOC has toxic and non-toxic volatile substances. Here, the toxic volatile substances include carbon monoxide, acetaldehyde, nitrogen dioxide, sulfur dioxide, acetylene, acrylonitrile, benzene, toluene or formaldehyde. The TVOC sensor 53 may determine whether the above-described toxic volatile substances are included in the air by measuring the total concentration of the volatile organic compounds.

According to an embodiment, the TVOC sensor 53 may be disposed inside the lower case 20. The TVOC sensor 53 may be disposed adjacent to the side ventilation hole 211 of the side cover 21. The TVOC sensor 53 may be fixed by the TVOC sensor cap 531 (shown in FIG. 3). The TVOC sensor cap 531 may not only fix the movement of the TVOC sensor 53, but also protect the TVOC sensor 53 from an external impact. The arrangement of the TVOC sensor 53 is exemplary and is not limited thereto.

According to an embodiment, the controller 100 may control the overall operation of the air quality measuring device 1. To that end, the controller 100 may include one or more of a central processing unit (CPU), an application processor (AP), or a communication processor (CP). The controller 100 may be a microcontroller (MCU).

The controller 100 may control hardware or software components connected to the controller 100 by driving an operating system or an application program, and may perform various data processing and operations. Further, the controller 100 may load a command or data received from at least one of other components on a volatile memory, process the command or data, and store various data in the non-volatile memory.

According to an embodiment, the controller 100 may receive the information about the air quality from the air quality detector 50 and transfer the information to an external electronic device using the wireless communication unit 120 or control the color of the light emitted from the light exiting surface 321 of the display 90 or the light guide 30 to provide visual information to the user.

The controller 100 may be provided on a first substrate (e.g., the first substrate 81 of FIG. 3).

According to an embodiment, the memory 110 may store data supporting various functions of the air quality measuring device 1. The memory 110 may store a plurality of application programs or applications used in the air quality measuring device 1, data and instructions for operating the air quality measuring device 1. At least some of these applications may be downloaded from an external server through wireless communication unit 120. Further, at least some of the application programs may be stored in the memory 110 from the time of shipping to perform default functions of the air quality measuring device 1. For example, the application program may be stored in the memory 110 and driven to perform an operation (or function) of the air quality measuring device 1 by the controller 100.

According to an embodiment, the display 90 may be controlled by the controller 100. The display 90 may control the display 90 to display information about air quality measured by the controller 100 using the air quality detector 50.

According to an embodiment, the wireless communication unit 120 may include one or more modules that enable wireless communication between the air quality measuring device 1 and a wireless communication system, between the air quality measuring device 1 and another device, or between the air quality measuring device 1 and an external server. According to an embodiment, the wireless communication unit 120 may include one or more modules connecting the air quality measuring device 1 to one or more networks. According to an embodiment, the wireless communication unit 120 may include at least one of a mobile communication module, a wireless internet module, a short-range communication module, or a location information module.

For example, the mobile communication module may transmit/receive a wireless signal to/from at least one of a base station, an external terminal, or a server on a mobile communication network established according to technical standards or communication methods for mobile communication. The wireless signals may include voice call signals, video call signals, or other various types of data according to transmission/reception of text/multimedia messages.

The wireless Internet module may be, but is not limited to WLAN (Wireless LAN), Wi-Fi (Wireless-Fidelity), Wi-Fi Direct, DLNA (Digital Living Network Alliance), WiBro (Wireless Broadband), WiMAX (World Interoperability for Microwave Access), HSDPA (High Speed Downlink Packet Access), HSUPA (High Speed Uplink Packet Access), LTE (Long Term Evolution), LTE-A (Long Term Evolution-Advanced), or 5G. Data may be transmitted and received according to at least one wireless Internet technology in the scope encompassing Internet technologies even not enumerated above.

The short-range communication module may be intended for short-range communication and may support short-range communication using at least one of Bluetooth, radio frequency identification (RFID), infrared data association (IrDA), ultra-wideband (UWB), ZigBee, near-field communication (NFC), Wi-Fi, Wi-Fi Direct, or wireless universal serial bus (USB) technology. The short-range communication module may support wireless communication between the air quality measuring device 1 and a wireless communication system, between the air quality measuring device 1 and another device, or between the air quality measuring device 1 and a network in which the other device is positioned through a short-range wireless communication network. Here, the wireless local area network may be a wireless personal area network.

The location information module may be a global positioning system (GPS) module or a Wi-Fi module as a module for obtaining the location of the air quality measuring device 1. When the air quality measuring device 1 utilizes the GPS module, the air quality measuring device 1 may receive information about the location of the air quality measuring device 1 using a signal transmitted from the GPS satellite. When the air quality measuring device 1 utilizes the Wi-Fi module, the air quality measuring device 1 may receive information about the location of the air quality measuring device 1 based on information about a wireless access point (AP) that transmits and receives a wireless signal to and from the Wi-Fi module.

Figure 5:
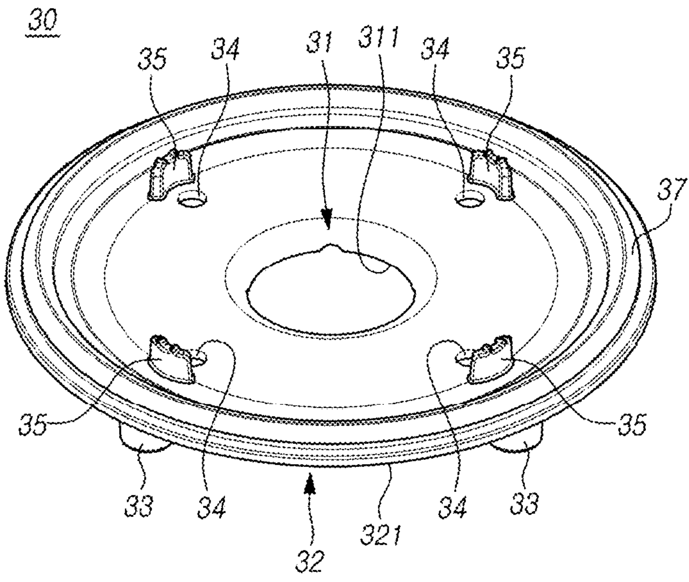
FIG. 5 is a top perspective view illustrating a light guide according to an embodiment of the disclosure.
Figure 6:
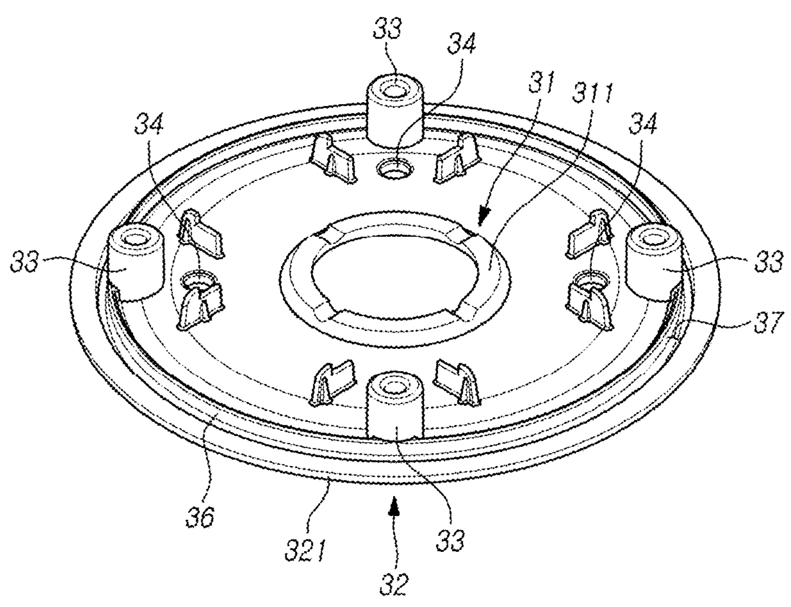
FIG. 6 is a bottom perspective view illustrating a light guide according to an embodiment of the disclosure.
Figure 7:
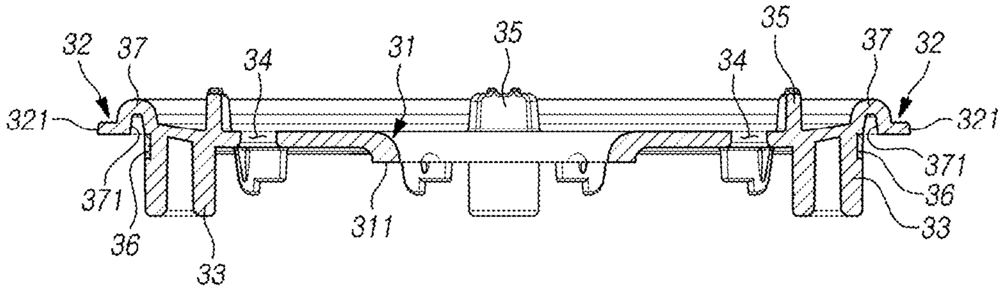
FIG. 7 is a cross-sectional view illustrating a light guide according to an embodiment of the disclosure.

FIG. 5 is a top perspective view illustrating a light guide according to an embodiment of the disclosure. FIG. 6 is a bottom perspective view illustrating a light guide according to an embodiment of the disclosure. FIG. 7 is a cross-sectional view illustrating a light guide according to an embodiment of the disclosure.

The light guide 30 illustrated in FIGS. 5 to 7 may be wholly or partially the same as the light guide 30 illustrated in FIGS. 2 and 3. A part of the configuration of the light guide 30 that overlaps the contents described with reference to FIGS. 2 and 3 will be omitted below. In the following description, the 'inside' or the 'outside' is determined with respect to the radial distance from the central portion of the light guide 30. For example, when the first component is positioned further inside than the second component, it may mean that the radial distance between the first component and the center portion is shorter than the radial distance between the second component and the center portion.

Referring to FIGS. 5 to 7, the light guide 30 may include a coupling boss 33, a coupling hole 34, a boss guide 35, a rib 36, or a groove 37. The light guide 30 may have a hollow circular shape in the middle.

According to an embodiment, the light guide 30 may have an inner portion 31 and an outer portion 32. The inner portion 31 may be a portion surrounding the hollow portion. The inner portion 31 and the outer portion 32 may have a circumferential shape. The light guide 30 may be provided to irradiate light emitted from the light source unit 40 to the outer portion 32. The light guide 30 may be formed of a material through which light may penetrate. For example, the light guide 30 may be formed of a translucent material.

According to an embodiment, the inner portion 31 may include a light entering surface 311. The inner portion 31 may be bent downward. Accordingly, the light entering surface 311 forming the cross section of the inner portion 31 may be provided to face downward.

According to an embodiment, at least one light source unit 40 may be provided at a portion adjacent to the inner portion 31. The light source unit 40 may transmit light into the light guide 30 by irradiating light toward the light entering surface 311. In other words, light may be incident on the light entering surface 311 and move outward in the radial direction.

According to an embodiment, the outer portion 32 may include a light exiting surface 321. Light incident from the inner portion 31 may move inside the light guide 30 and be emitted to the light exiting surface 321 of the outer portion 32. The outer portion 32 may be provided between an upper case (e.g., the upper case 10 of FIG. 1) and a lower case (e.g., the lower case 20 of FIG. 1) to be visible from the outside. Accordingly, the light emitted from the outer portion 32 may be viewed from the outside by the user.

According to an embodiment, the rib 36 may be formed to protrude from one surface of the light guide 30. The overall shape of the rib 36 may be a circumferential shape, but is not limited thereto. The rib 36 may be positioned around the outer portion 32 of the light guide 30. In other words, the rib 36 may be positioned close to the outer portion 32 of the light guide 30.

According to an embodiment, the rib 36 may be positioned between the outer portion 32 of the light guide 30 and the coupling boss 33. Specifically, the coupling boss 33, the rib 36, and the outer portion 32 may be sequentially positioned based on the distance from the center of the light guide 30. According to an embodiment, the rib 36 may be provided so that a portion of the rib 36 contacts a radially outer portion of the coupling boss 33 as illustrated. When the rib 36 and the coupling boss 33 come into contact with each other, the rib 36 and the coupling boss 33 may be integrally formed at the contacting portion.

According to an embodiment, the rib 36 may be disposed inside the coupling boss 33. According to an embodiment, the rib 36 may be disposed along a circumferential shape passing through the plurality of coupling bosses 33.

When light passes through the inside of the light guide 30, light may be concentrated toward where more media are present. In the case of the light guide 30, a large amount of light may be concentrated on the protruding coupling boss 33. As a result, light emitted from a portion of the light exiting surface 321 close to the coupling boss 33 may be brighter than light emitted from a portion of the light exiting surface 321 far from the coupling boss 33, thereby reducing uniformity of luminance. In particular, as in the disclosure, when the coupling boss 33 is positioned close to the outer portion 32, the non-uniformity of luminance may be increased. In the disclosure, by forming the rib 36, it may be possible to prevent light from being concentrated on the coupling boss 33, and overall disperse light to the rib 36. As a result, even if the coupling boss 33 is positioned adjacent to the outer portion 32, uniformity of luminance may be enhanced by the rib 36.

According to an embodiment, the groove 37 may be provided between the outer portion 32 of the light guide 30 and the coupling boss 33. The groove 37 may have a circumferential shape, but is not limited thereto. The groove 37 may be integrally formed to have a circumferential shape as illustrated, but a plurality of grooves 37 may be formed outside the coupling boss 33 to be spaced apart from each other by a predetermined interval in the circumferential direction. The groove 37 may be positioned outside the rib 36, but is not limited thereto. The groove 37 may be formed as a portion of the light guide 30 protrudes to the surface opposite to the surface where the rib 36 protrudes, but is not limited thereto.

Light passing through the light guide 30 may mainly move inside the light guide 30 as a medium. The light may move from the light entering surface 311 to the light exiting surface 321 while being reflected on a boundary surface (e.g., the upper surface or the lower surface of the light guide 30) inside the light guide 30. When the incident angle is larger than a predetermined angle when the light hits the boundary surface (e.g., the upper surface or the lower surface of the light guide 30), the light may be transmitted to the outside without being reflected. Using these characteristics, some of the light may be transmitted from the inside of the light guide 30 to the groove 37. In other words, some of the light passing through the inside of the light guide 30 may pass through the groove 37 and then be transmitted back to the inside of the outer light guide 30 to move to the light exiting surface 321. As light is refracted while passing through the groove 37, uniformity of luminance may be enhanced.

Figure 8:
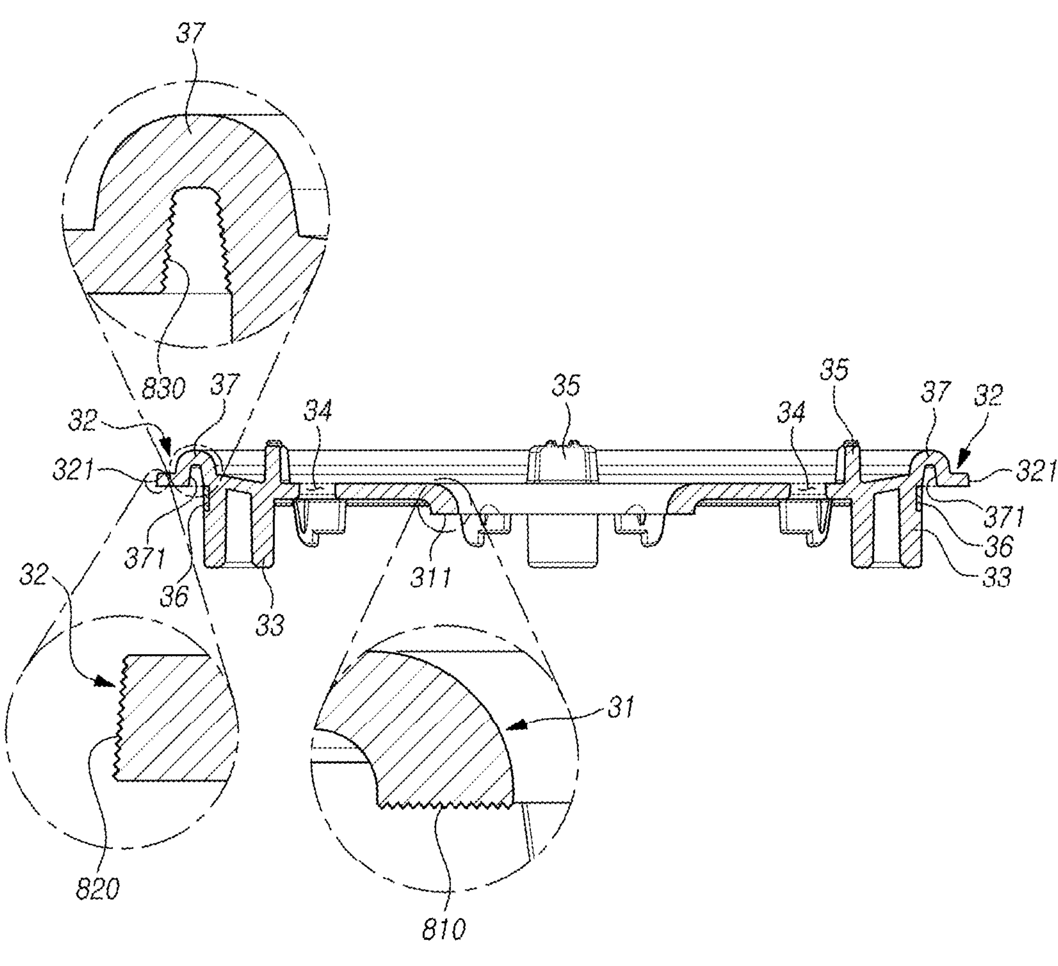
FIG. 8 is a view illustrating a state in which a protrusion-and-depression shape is applied to a portion of a light guide according to an embodiment of the disclosure.

FIG. 8 is a view illustrating a state in which a protrusion-and-depression shape is applied to a portion of a light guide according to an embodiment of the disclosure.

The light guide 30 illustrated in FIG. 8 may be identical in whole or part to the configuration of the light guide 30 of FIGS. 5 to 7.

According to an embodiment, a textured surface may be applied to the surface of the light entering surface 311 of the light guide 30. In other words, a first uneven surface (e.g., protrusion-and-depression, irregular surface, rough surface, rugged surface, textured surface, or grooved surface) 810 may be applied to the surface of the light entering surface 311. As illustrated, a protrusion shape of the first uneven surface 810 may be triangular but is not limited thereto, and irregularly shaped protrusions may be applied to disperse light. As another example, a protrusion shape of the first uneven surface 810 may be semicircular or hemispherical.

According to an embodiment, a textured surface may be applied to the surface of the light exiting surface 321 of the light guide 30. In other words, a second uneven surface (e.g., protrusion-and-depression, irregular surface, rough surface, rugged surface, textured surface, or grooved surface) 820 may be applied to the surface of the light exiting surface 321. As illustrated, a protrusion shape of the second uneven surface 820 may be triangular, but is not limited thereto, and irregularly shaped protrusions may be applied to disperse light. As another example, a protrusion shape of the second uneven surface 820 may be semicircular or hemispherical.

According to an embodiment, a textured surface may be applied to the surface of the inner surface 371 of the groove 37. In other words, a third uneven surface (e.g., protrusion-and-depression, irregular surface, rough surface, rugged surface, textured surface, or grooved surface) 830 may be applied to the surface of the inner surface 371 of the groove 37. Here, the inner surface 371 of the groove 37 may be a surface through which light transferred from the light entering surface 311. As illustrated, a protrusion shape of the third uneven surface 830 may be triangular, but is not limited thereto, and irregularly shaped protrusions may be applied to disperse light. As another example, a protrusion shape of the third uneven surface 830 may be semicircular or hemispherical.

As described above, while the light is moved from the light source unit (e.g., the light source unit 40 of FIG. 3) to the light exiting surface 321 of the light guide 30, the textured surface may be applied to the surface of the portion where light is transmitted from the inside of the light guide 30 to the outside of the light guide 30 or where light is transmitted from the outside of the light guide 30 to the inside of the light guide 30. Accordingly, light may be irregularly refracted and dispersed by the textured surface while passing through the light entering surface 311, the light exiting surface 321, and/or the inner surface 371 of the groove 37. This may prevent light from being concentrated on a specific portion (e.g., the coupling boss 33) of the light guide 30, and may also enhance uniformity of luminance of the light exiting surface 321 by dispersing light concentrated on the specific portion (e.g., the coupling boss 33).

Figure 9:
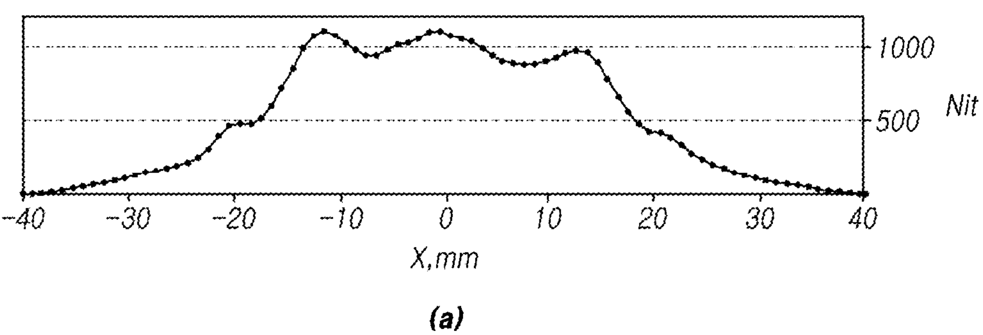
FIG. 9 is a graph illustrating luminance uniformity of a light guide according to an embodiment of the disclosure.
Figure 9:
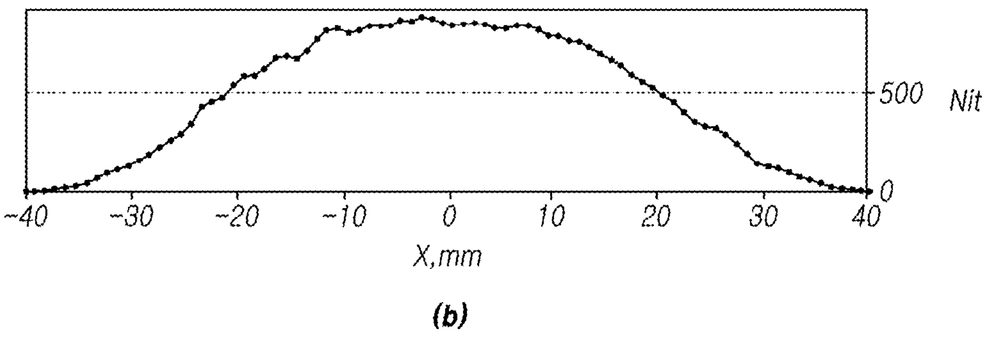

FIG. 9 is a graph illustrating luminance uniformity of a light guide according to an embodiment of the disclosure.

FIG. 9(*a*) is a graph illustrating uniformity of luminance in a conventional light guide in which coupling bosses protrudes upward and downward, respectively, to vertically couple the upper case 10 and the lower case 20. FIG. 9(*b*) is a graph illustrating uniformity of luminance of the light guide 30 according to an embodiment of the disclosure.

In the light guide 30 according to an embodiment of the disclosure, compared to the conventional light guide, the configuration of the coupling boss protruding upward is replaced with the coupling hole 34, and components such as a rib 36 and a groove 37 are added. In the light guide 30 according to an embodiment of the disclosure, since the coupling boss 33 is disposed outside the coupling hole 34 in the light guide 30, it may be disposed closer to the outer portion 32 than the coupling boss formed in the conventional light guide.

Referring to FIG. 9(*a*), the luminance uniformity of the conventional light guide is about 36.9% with respect to ±25 mm. Referring to FIG. 9(*b*), the luminance uniformity of the light guide 30 according to an embodiment of the disclosure is about 70% with respect to ±25 mm. As identified in the experimental example, the light guide 30 according to an embodiment of the disclosure may have an effect of enhancing luminance uniformity by about twice as much as that of the conventional light guide.

Figure 10:
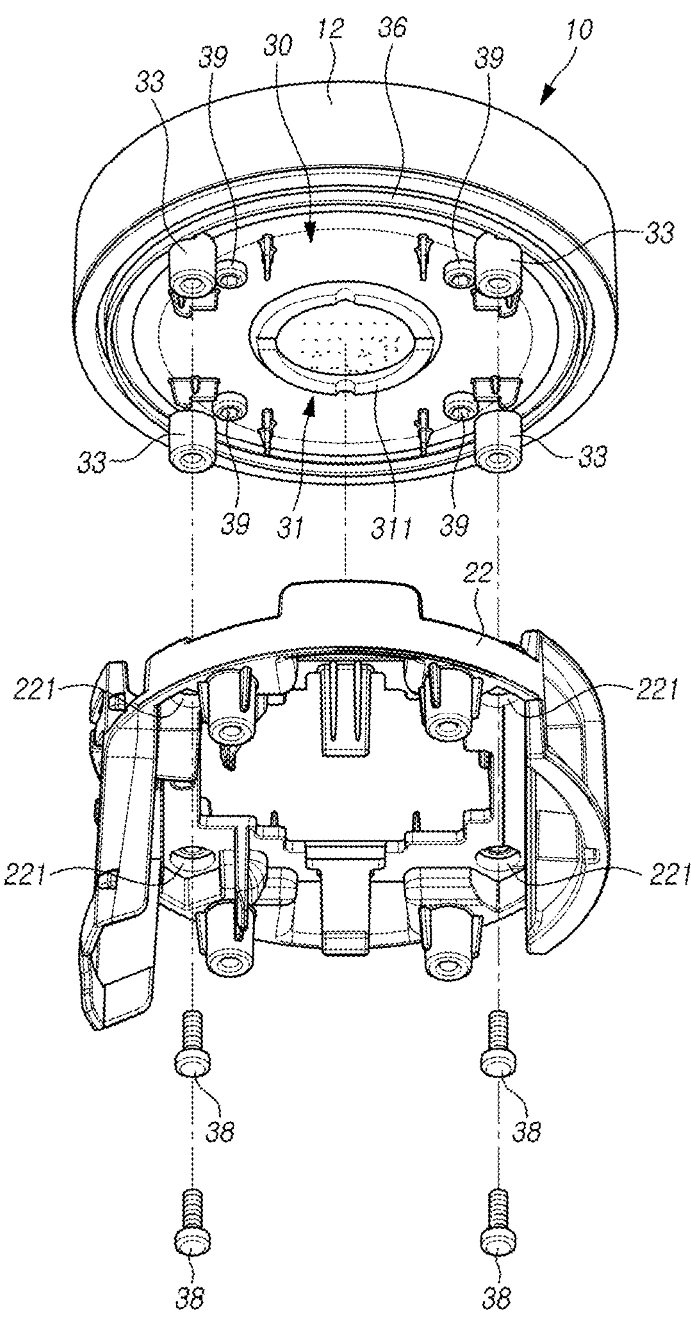
FIG. 10 is a view illustrating a process of disassembling the lower case of the air quality measuring device of FIG. 1.

FIG. 10 is a view illustrating a process of disassembling the lower case of the air quality measuring device of FIG. 1.

FIG. 10 is a view for describing a process of disassembling the air quality measuring device 1. The upper case 10, the light guide 30, and the lower frame 22 are illustrated, and other internal components are omitted for convenience of description. The upper case 10, the light guide 30, and the lower frame 22 illustrated in FIG. 10 may be wholly or partially the same as the upper case 10, the light guide 30, or the lower frame 22 illustrated in FIGS. 2 and 3.

According to an embodiment, the air quality measuring device 1 may be sequentially disassembled from a lower portion. In the drawings, a process in which the first lower frame 22 of the lower case is separated from the light guide 30 is illustrated. The first lower frame 22 and the light guide 30 may be separated by separating the first coupling hole 221 of the first lower frame 22 and the first screw 38 fastened to the coupling boss 33 of the light guide 30. In this case, the head portion of the first screw 38 faces downward.

Figure 11:
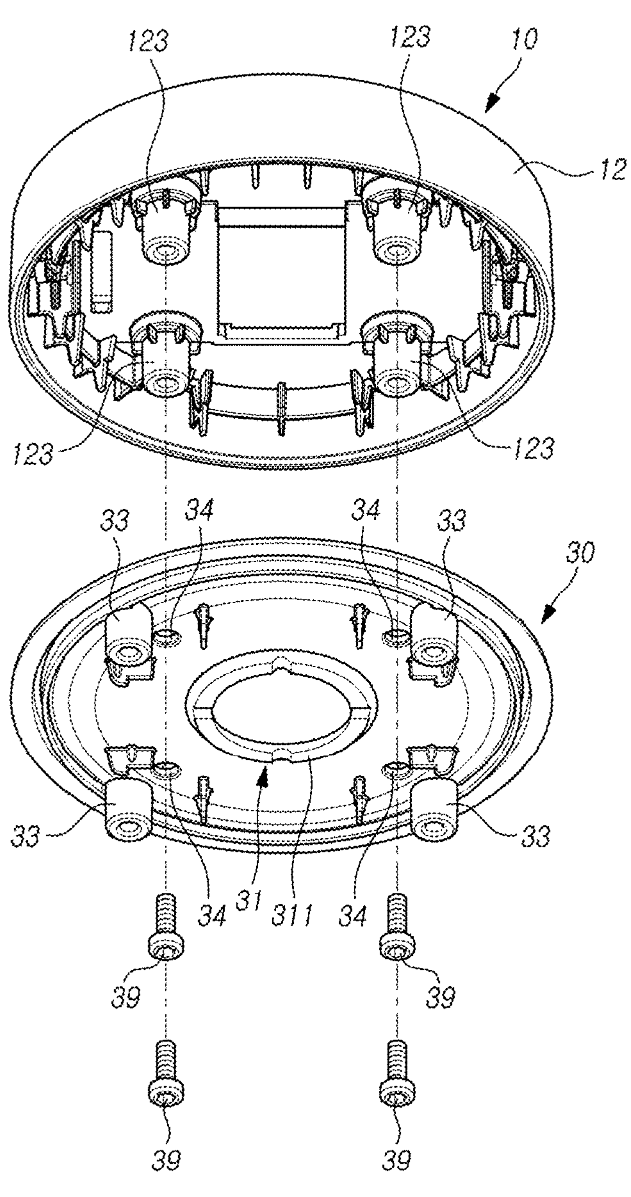
FIG. 11 is a view illustrating a process of disassembling the light guide in FIG. 10.

FIG. 11 is a view illustrating a process of disassembling the light guide in FIG. 10.

FIG. 11 is a view for describing a process in which the light guide 30 is disassembled from the upper case 10. The upper case 10 and the light guide 30 illustrated in FIG. 11 may be wholly or partially the same as the upper case 10 and the light guide 30 illustrated in FIGS. 2 and 3.

According to an embodiment, in the light guide 30, the coupling boss 33 may be disassembled from the upper case 10. The upper frame 12 and the light guide 30 may be separated by separating the upper coupling boss 123 of the upper frame 12 and the second screw 39 fastened to the coupling hole 34 of the light guide 30. As the head portion of the second screw 39 faces upward, the user should first disassemble the window 11 of the upper case 10 and then disassemble the upper frame 12 and the light guide 30. In this case, while the window 11 is disassembled from the upper frame 12, external damage may occur to the window 11 or the upper frame 12. In one embodiment, since the head portion of the second screw 39 faces downward, the user may immediately disassemble the light guide 30 without the need for first disassembling the window 11 of the upper case 10. Therefore, it is possible to prevent damage to the exterior of the upper case 10.

Figure 12:
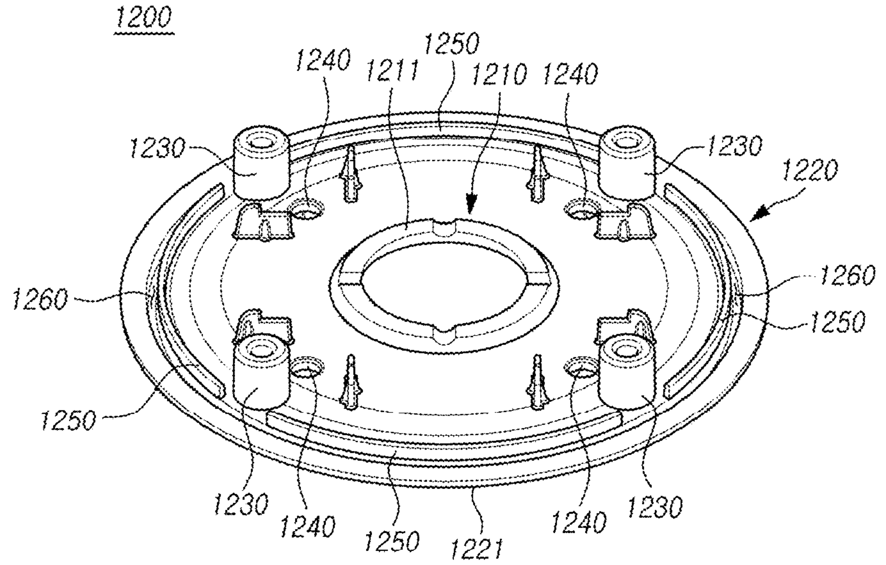
FIG. 12 is a view illustrating a light guide according to a second embodiment of the disclosure.

FIG. 12 is a view illustrating a light guide according to a second embodiment of the disclosure.

The configuration of the light guide 1200 according to the second embodiment illustrated in FIG. 12 may be partially the same as the configuration of the light guide 30 illustrated in FIGS. 5 to 7. The light guide 1200 according to the second embodiment of FIG. 12 may be coupled to the upper case 10 and the lower case 20 of the air quality measuring device 1 illustrated in FIGS. 1 to 3.

Referring to FIG. 12, the light guide 1200 according to the second embodiment may include an inner portion 1210, an outer portion 1220, a coupling boss 1230, a coupling hole 1240, a rib 1250, and a groove 1260. The inner portion 1210, the outer portion 1220, the coupling boss 1230, the coupling hole 1240, and the groove 1260 of the light guide 1200 according to the illustrated second embodiment may be wholly or partially the same as the inner portion 31, the outer portion 32, the coupling boss 33, the coupling hole 34, and the groove 37 of the light guide 30 illustrated in FIG. 5. Therefore, a description of a configuration overlapping the configuration described with reference to FIG. 5 will be omitted.

According to an embodiment, a plurality of the ribs 1250 may be provided in the light guide 1200. The plurality of the ribs 1250, respectively, may be arranged to be spaced apart from each other with a coupling boss 1230 therebetween. The rib 1250 may have an arc shape as illustrated. Therefore, the four ribs 1250 illustrated may have an overall substantially circular (or cylindrical) shape. According to an embodiment, the rib 1250 may have a linear shape. In this case, the overall shape of the linear ribs 1250 disposed between the plurality of coupling bosses 1230 may be substantially polygonal.

According to an embodiment, the rib 1250 may be provided to surround a portion that does not overlap the coupling boss 33, outside the coupling boss 1230. The rib 1250 is a component for preventing light transferred from the light source unit (e.g., the light source unit 40 of FIG. 3) from being concentrated on the coupling boss 1230 to make luminance uneven, and may be provided only in an area other than the area overlapping the coupling boss 1230 to have an effect of dispersing light. In other words, by omitting the rib 1250 around the coupling boss 1230 in which light is already concentrated, it is possible to more effectively prevent light from being concentrated on the coupling boss 1230 side.

According to an embodiment, even if the groove 1260 is omitted from the light guide 1200, uniformity of luminance may be enhanced by the rib 1250.

Figure 13:
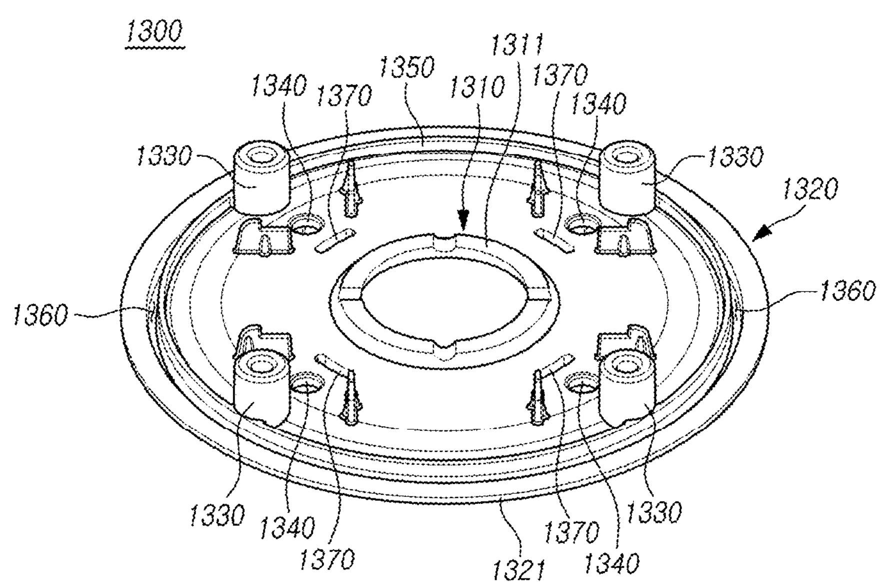
FIG. 13 is a view illustrating a light guide according to a third embodiment of the disclosure.

FIG. 13 is a view illustrating a light guide according to a third embodiment of the disclosure.

The configuration of the light guide 1300 according to the third embodiment illustrated in FIG. 13 may be partially the same as the configuration of the light guide 30 illustrated in FIGS. 5 to 7. The light guide 1300 according to the third embodiment of FIG. 13 may be coupled to the upper case 10 and the lower case 20 of the air quality measuring device 1 illustrated in FIGS. 1 to 3.

Referring to FIG. 13, the light guide 1300 according to the third embodiment may include an inner portion 1310, an outer portion 1320, a coupling boss 1330, a coupling hole 1340, a rib 1350, and a groove 1360. The inner portion 1310, the outer portion 1320, the coupling boss 1330, the coupling hole 1340, the rib 1350, and the groove 1360 of the light guide 1300 according to the illustrated third embodiment may be wholly or partially the same as the inner portion 31, the outer portion 32, the coupling boss 33, the coupling hole 34, or the groove 37 of the light guide 30 illustrated in FIG. 5. Therefore, a description of a configuration overlapping the configuration described with reference to FIG. 5 will be omitted.

According to an embodiment, the light guide 1300 may further include a through hole 1370. The through hole 1370 may be formed radially inside the coupling boss 1330. For example, as many through holes 1370 as the number of coupling bosses 1330 may be formed radially inside the coupling bosses 1330. The through hole 1370 may be curved as illustrated, but is not limited thereto.

Light emitted by the light source unit (e.g., the light source unit 40 of FIG. 3) may move radially outward from the inner portion 1310. Here, some of the light directed to the through hole 1370 may move through the through hole 1370 or bypass the through hole 1370. Some light passing through the through hole 1370 may be dispersed by the shape of the through hole 1370. Accordingly, the through hole 1370 may serve to prevent light from being concentrated on the coupling boss 1330 in advance. As a result, uniformity of luminance may be enhanced.

According to an embodiment, even if the rib 1350 or the groove 1360 is omitted from the light guide 1300, uniformity of luminance may be enhanced by the through hole 1370.

According to an embodiment, the inner surface of the through hole 1370 may be textured. In other words, protrusions and depressions may be applied to make the inner surface of the through hole 1370 an irregular surface.

Figure 14:
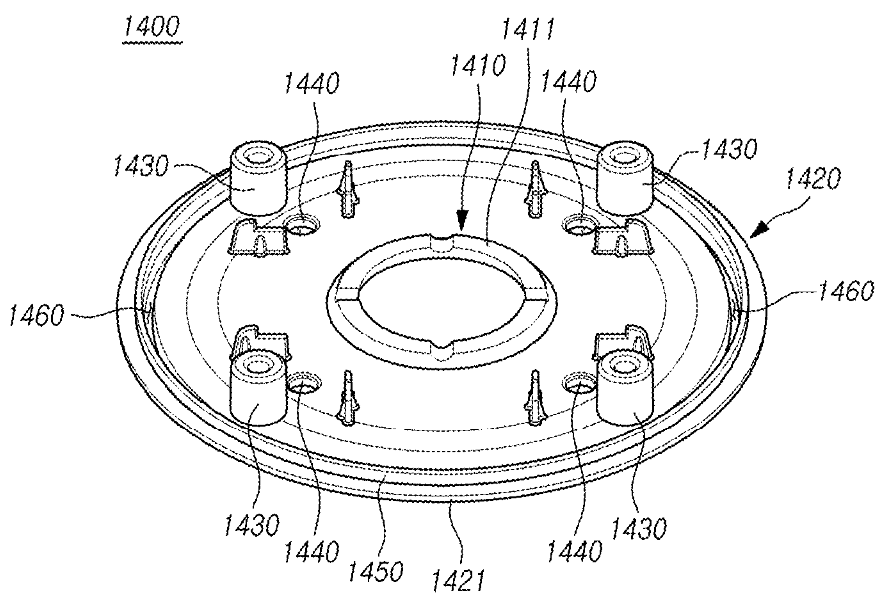
FIG. 14 is a view illustrating a light guide according to a fourth embodiment of the disclosure.

FIG. 14 is a view illustrating a light guide according to a fourth embodiment of the disclosure.

The configuration of the light guide 1400 according to the fourth embodiment illustrated in FIG. 14 may be partially the same as the configuration of the light guide 30 illustrated in FIGS. 5 to 7. The light guide 1300 according to the fourth embodiment of FIG. 14 may be coupled to the upper case 10 and the lower case 20 of the air quality measuring device 1 illustrated in FIGS. 1 to 3.

Referring to FIG. 14, the light guide 1400 according to the fourth embodiment may include an inner portion 1410, an outer portion 1420, a coupling boss 1430, a coupling hole 1440, a rib 1450, and a groove 1460. The inner portion 1410, the outer portion 1420, the coupling boss 1430, the coupling hole 1440, the rib 1450, and the groove 1460 of the light guide 1400 according to the illustrated fourth embodiment may be wholly or partially the same as the inner portion 31, the outer portion 32, the coupling boss 33, the coupling hole 34, and the groove 37 of the light guide 30 illustrated in FIG. 5. Therefore, a description of a configuration overlapping the configuration described with reference to FIG. 5 will be omitted.

According to an embodiment, the rib 1450 may be disposed outside the groove 1460. In other words, the light guide 1400 according to the fourth embodiment is different from the light guide 30 of FIG. 5 in the arrangement relationship between the rib 1450 and the groove 1460. The light moving from the light entering surface 1411 may be dispersed while passing through the groove 1460, so that the light concentrated on the coupling boss 1430 may be primarily dispersed, and after passing through the groove 1460, the light may be secondarily dispersed so that the light is uniformly distributed by the rib 1450. As a result, uniformity of luminance may be enhanced.

The terms as used herein are provided merely to describe some embodiments thereof, but are not intended to limit the disclosure. As used herein, the singular forms "a," "an," and "the" are intended to include the plural forms as well, unless the context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, the term 'and/or' should be understood as encompassing any and all possible combinations by one or more of the enumerated items. As used herein, the terms "include," "have," and "comprise" are used merely to designate the presence of the feature, component, part, or a combination thereof described herein, but use of the term does not exclude the likelihood of presence or adding one or more other features, components, parts, or combinations thereof. As used herein, the terms "first" and "second" may modify various components regardless of importance and/or order and are used to distinguish a component from another without limiting the components.

As used herein, the terms "configured to" may be interchangeably used with the terms "suitable for," "having the capacity to," "designed to," "adapted to," "made to," or "capable of" depending on circumstances. The term "configured to" does not essentially mean "specifically designed in hardware to." Rather, the term "configured to" may mean that a device can perform an operation together with another device or parts. For example, a 'device configured (or set) to perform A, B, and C' may be a dedicated device to perform the corresponding operation or may mean a general-purpose device capable of various operations including the corresponding operation.

Meanwhile, the terms "upper side", "lower side", and "front and rear directions" used in the disclosure are defined with respect to the drawings, and the shape and position of each component are not limited by these terms.

In the disclosure, the above-described description has been made mainly of specific embodiments, but the disclosure is not limited to such specific embodiments, but should rather be appreciated as covering all various modifications, equivalents, and/or substitutes of various embodiments.

What is claimed is:

1. An air quality measuring device, comprising:
- an upper case;
- a lower case disposed under the upper case;
- a circular light guide disposed between the upper case and the lower case, having an outer portion and an inner portion, and comprising a coupling boss positioned around the outer portion and protrudes downward to couple with the lower case and a coupling hole provided to couple with the upper case; and
- a light source unit positioned on the inner portion,
- wherein the circular light guide forms a light exiting surface on the outer portion, and includes a rib formed to protrude to one surface surrounded by the outer portion.

2. The air quality measuring device of claim 1, wherein the rib is positioned between the outer portion and the coupling boss.

3. The air quality measuring device of claim 1, wherein the rib partially contacts radially outside of the coupling boss.

4. The air quality measuring device of claim 1, wherein the circular light guide further includes a groove provided between the outer portion and the coupling boss.

5. The air quality measuring device of claim 4, wherein the groove has an inner surface with an uneven shape.

6. The air quality measuring device of claim 4, wherein the groove is positioned outside the rib.

7. The air quality measuring device of claim 1, wherein the outer portion is provided between the upper case and the lower case to be visible from outside.

8. The air quality measuring device of claim 1, wherein the inner portion or the outer portion has a surface with a uneven shape.

9. The air quality measuring device of claim 1, wherein the circular light guide further includes a through hole formed radially inside of the coupling boss.

10. The air quality measuring device of claim 1,
- wherein the circular light guide further includes a plurality of screws coupled to the coupling boss and the coupling hole, and
- wherein the plurality of screws are coupled to allow a screw head to face downward.

11. The air quality measuring device of claim 1,
wherein a plurality of coupling bosses are configured, and
wherein a plurality of ribs are respectively disposed at intervals of the plurality of coupling bosses.

12. The air quality measuring device of claim 1, wherein the circular light guide is coupled to the upper case by a screw fastened from a lower side to an upper side such that a head portion of the screw faces downward.

13. A circular light guide, comprising:
an inner portion having a light entering surface through which light enters;
an outer portion having a light exiting surface through which light exits;
a coupling boss positioned around the outer portion and provided to protrude upward or downward;
a rib formed to protrude from one surface of the circular light guide surrounded by the outer portion, the rib being circumferential and positioned radially between the outer portion and the coupling boss; and
a circumferential groove provided between the outer portion and the coupling boss.

14. The circular light guide of claim 13, wherein the inner portion or the outer portion has a surface with an uneven shape.

15. An air quality measuring device, comprising:
an upper case;
a lower case disposed under the upper case;
a circular light guide disposed between the upper case and the lower case, having an outer portion and an inner portion, and having a coupling boss positioned around the outer portion to couple with the upper case or the lower case:
a light source unit positioned on the inner portion, wherein the circular light guide forms a light exiting surface on the outer portion, and includes a rib formed to protrude to one surface surrounded by the outer portion;
an air quality detector disposed between the upper case and the lower case; and
a controller configured to communicate with the air quality detector and the light source unit,
wherein the controller is configured to control an operation of the light source unit based on data received from the air quality detector.

16. The air quality measuring device of claim 15, wherein the operation of the light source unit includes a color of a light emitted by the light source unit.

* * * * *